(12) United States Patent
Lines

(10) Patent No.: US 8,680,053 B2
(45) Date of Patent: Mar. 25, 2014

(54) IMPROVING RENAL FUNCTION WITH QUERCETIN-CONTAINING COMPOSITIONS

(75) Inventor: Thomas Christian Lines, Luxembourg (LU)

(73) Assignee: Quercegen Pharmaceuticals LLC, Marlborough, MA (US)

( * ) Notice: Subject to any disclaimer, the term of this patent is extended or adjusted under 35 U.S.C. 154(b) by 882 days.

(21) Appl. No.: 12/169,869

(22) Filed: Jul. 9, 2008

(65) Prior Publication Data

US 2010/0010005 A1    Jan. 14, 2010

(51) Int. Cl.
*A61K 38/00*    (2006.01)

(52) U.S. Cl.
USPC ........................................... 514/15.4

(58) Field of Classification Search
None
See application file for complete search history.

(56) References Cited

U.S. PATENT DOCUMENTS

| | | | | |
|---|---|---|---|---|
| 5,849,569 | A * | 12/1998 | Davies | 435/288.3 |
| 6,103,756 | A * | 8/2000 | Gorsek | 514/458 |
| 6,210,701 | B1 * | 4/2001 | Darland et al. | 424/439 |
| 6,821,536 | B2 * | 11/2004 | Lines et al. | 426/73 |
| 6,995,166 | B1 | 2/2006 | Giordano et al. | |
| 2004/0126461 | A1 | 7/2004 | Lines et al. | |

FOREIGN PATENT DOCUMENTS

| | | |
|---|---|---|
| CN | 1132643 | 10/1996 |
| CN | 1883695 | 12/2006 |
| CN | 101032619 | 9/2007 |
| CN | 101112603 | 1/2008 |
| CN | 101199834 | 6/2008 |
| DE | 102009015917 | 10/2010 |
| EP | 0742012 | 11/1996 |
| WO | 03-037246 | 5/2003 |
| WO | 2004-037015 | 5/2004 |
| WO | 2004-037018 | 5/2004 |
| WO | 2004-062672 | 7/2004 |
| WO | WO 2004062672 A1 * | 7/2004 |
| WO | WO 2008-011363 | 1/2008 |

OTHER PUBLICATIONS

Holt, Steve et al. "The potential usefulness of vitamin C as an antioxidant." Intensive Care Med, 2002, vol. 28.
Nobuaki, Eto et al. Nicotinamide prevents the development of hyperphosphataemia by suppressing intestinal sodium-dependent phosphate transporter in rats with adenine-induced renal failure. "Nephrol Dial Transplant" 2005, vol. 20.
Zal, Fatemeh et al. "Comparison of the effects of Vitamin E and/or Quercetin in attenuating chronic cyclosporine A-induced nephrotoxicity in male rats." Clinical and Experimental Pharmacology and Physiology. 2007, vol. 34.
Satyanarayana P S V et al., "Quercetin, a bioflavonoid, protects against oxidative stress-related renal dysfunction by cyclosporine in rats," in Methods and Findings in Experimental and Clinical Pharmacology, Barcelona: Prous Science—Thomson Reuters, 1979-2010 Anfangs: Barcelona: Prous, ES, vol. 23, No. 4, May 1, 2001, pp. 175-181.
Chander V et al., "Reversal of experimental myoglobinuric acute renal failure in rats by quercetin, a bioflavonoid," Pharmacology, S. Karger AG, CH, vol. 73, No. 1, Jan. 1, 2005, pp. 49-56.
Anjaneyulu Muragundla et al., "Quercetin, an antioxidant bioflavonoid, attenuates diabetic nephropathy in rats," Clinical and Experimental Pharmacology & Physiology Apr. 2004, vol. 31, No. 4, Apr. 2004, pp. 244-248.
Yusuksawad Mariem S et al., "Changes in renal hemodynamics in streptozotocin-induced diabetic rats with L ascorbic acid supplementation," Clinical Hemorheology and Microcirculation, IOS Press, Amsterdam, NL, vol. 34, No. 3, Jan. 1, 2006, pp. 391-399.
Huang Han-Yao et al., "The effects of vitamin C supplementation on serum concentrations of uric acid—Results of a randomized controlled trial," Arthritis & Rheumatism, vol. 52, No. 6, Jun. 2005, pp. 1843-1847.
"Supplementary European search report" issued in EP Application No. 09795103 Applicant: Quercegen Pharmaceuticals, LLC., Date of Mailing: Dec. 17, 2013, pp. 1-3.

* cited by examiner

*Primary Examiner* — Anand Desai
*Assistant Examiner* — Melissa Mercier
(74) *Attorney, Agent, or Firm* — Cesari and McKenna, LLP

(57) ABSTRACT

This invention relates to a method of improving renal function by administering to a subject in need thereof an effective amount of a composition containing quercetin, vitamin C, vitamin B3, and folic acid.

13 Claims, No Drawings

IMPROVING RENAL FUNCTION WITH QUERCETIN-CONTAINING COMPOSITIONS

BACKGROUND

It is known that certain natural antioxidants, such as quercetin, inhibit both acute and chronic phases of free-radical induced diseases. Further, some natural antioxidants exhibit synergy in their reactions with biologically relevant oxygen species, e.g., hydroxyl radicals, superoxides, oxysulfurs, sulfur dioxide, and nitrogen dioxide.

SUMMARY

The present invention features a method of improving renal function by administering to a subject in need thereof an effective amount of a composition containing quercetin, vitamin C, and vitamin B3. The weight ratio between quercetin, vitamin C, and vitamin B3 can be 1:0.2-2.5:0.02-1 , e.g., 1:1:0.04:0.8.

Preferably, the composition used in the method of this invention further contains folic acid. The weight ratio between quercetin, vitamin C, vitamin B3, and folic acid can be 1:0.2-2.5:0.02-1:0.2-2 (mg/mg/mg/mcg), e.g., 1:0.5-1:0.02-0.2:0.5-1 (mg/mg/mg/mcg) or 1:1:0.04:0.8 (mg/mg/mg/mcg). The unit "mcg" is an abbreviation of microgram.

In the method of this invention, the subject in need of the treatment can be identified via routine medical practices and administered each day with an amount of the composition that provides 500-2000 mg quercetin (e.g., 500 mg quercetin, 1000 mg quercetin, 1500 mg quercetin, or 2000 mg quercetin), and if desired, 500-2000 mg vitamin C (e.g., 500-1500 mg or 500-1000 mg), 20-60 mg vitamin B3 (e.g., 20-40 mg), and 400-800 mcg. In one example, the subject is administered per day with an amount of the composition that provides 500 mg quercetin, 500 mg vitamin C, 20 mg vitamin B3, and 400 mcg folic acid. In another example, the subject is administered per day with 1000 mg quercetin, 1000 mg vitamin C, 40 mg vitamin B3, and 800 mcg folic acid in combination The composition used in the method of this invention, either in dry form (e.g., powder or tablet) or in liquid form (e.g., beverage or syrup), can be a dietary supplement or a pharmaceutical formulation. The dietary supplement or the pharmaceutical formulation can be in the form of a tablet, a capsule, a soft chew, or a gel. The composition can also be a food product. Examples include tea (e.g., a tea drink and the contents of a tea bag), soft drinks, juice (e.g., a fruit extract and a juice drink), milk, coffee, jelly, ice cream, yogurt, cookies, cereals, chocolates, and snack bars.

The composition can also be a pharmaceutical composition containing the above-mentioned four ingredients and a pharmaceutically acceptable carrier, or a soft chew composition containing the four ingredients and various inactive additives (e.g., excipients, sweeteners, and artificial flavors).

Also within the scope of this invention is the use of any of the compositions described above for improving renal function and for the manufacture of a medicament for improving renal function.

The details of one or more embodiments of the invention are set forth in the description below. Other features, objects, and advantages of the invention will be apparent from the description and from the claims.

DETAILED DESCRIPTION

The present invention is based on the unexpected discovery that administering to a human subject a composition containing quercetin, vitamin C, vitamin B3, and folic acid results in increase of the kidney glomerular filtration rate and reduction of creatinine kinase activity, an indication of renal function improvement.

Accordingly, described herein is a method of improving renal function with an effective amount of a composition containing quercetin, vitamin C, vitamin B3, and preferably folic acid. Renal function refers to the excretory and blood purification or filtration function of the kidney. It is commonly evaluated by measuring the glomerular filtration rate (GFR), i.e., the flow rate of filtered fluid through the kidney, or the creatinine clearance rate ($C_{Cr}$), i.e., the volume of blood plasma that is cleared of creatinine per unit time. Increase of either GFR or $C_{Cr}$ indicates improvement in renal function. The term "effective amount," as used herein, refers to the amount of each active agent which, upon administration with one or more other active agents to a subject in need thereof, is required to confer therapeutic effect on the subject. Effective amounts vary, as recognized by those skilled in the art, depending on route of administration, excipient usage, and the co-usage with other active agents.

It is known that, upon oral administration, a combination of quercetin, vitamin B3, and vitamin C results in a significantly higher quercetin concentration in plasma than quercetin alone. More specifically, a combination of quercetin, vitamin B3, and vitamin C maintains quercetin levels in plasma up to five times those of quercetin alone or a combination of quercetin and vitamin B3; and that a combination of quercetin, vitamin B3, and vitamin C results in a quercetin half life in plasma twice as long as that of quercetin alone and about one and a half times that of a combination of quercetin and vitamin B3. See US 20080015247 and US20080032987.

The weight ratio between quercetin, vitamin C, vitamin B3, and folic acid in a composition used in the method of this invention can be 1:0.2-2.5:0.02-1:0.2-2 (mg/mg/mg/mcg), or any ratio in between. For example, the weight ratio can be 1:0.5-1:0.02-0.2:0.5-1 (mg/mg/mg/mcg), or 1:1:0.04:0.8 (mg/mg/mg/mcg). Preferably, a subject is administered, once or periodically per day, with the composition in an amount that provides 250 mg to 2000 mg (e.g., 500 mg to 1500 mg, or 500 mg to 1000 mg) of quercetin, which can be quercetin aglycon, isoquercetin, or a combination thereof.

The term "quercetin" refers to quercetin aglycon, a quercetin derivative, or a mixture thereof. Quercetin derivatives include, but are not limited to quercetin-3-O-glucoside (also known as isoquercetin), quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, e.g., glucoronates, sulphates, and methylates, which are absorbed in the body. The quantity of quercetin mentioned above refers to that of quercetin aglycon or its derivatives, and any quercetin moiety of a quercetin derivative formed via digestion. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil).

"Vitamin B3" mentioned herein includes vitamin B3 in its various forms, including niacinamide, nicotinic acid, nicotinamide, inositol hexaniacinate.

"Vitamin C" mentioned herein includes vitamin C (i.e., L-ascorbic acid, D-ascorbic acid, or both) and its salts (e.g., sodium ascorbate).

"Folic acid" mentioned herein includes vitamin B9, folate, pteroylglutamic acid, and their derivatives, e.g., methylfolate.

The composition used in the method of this invention can be in various forms. For example, it can be a soft chew composition that includes quercetin, niacinamide, ascorbic acid, sodium ascorbate, sugar, corn syrup, sucralose, soy lecithin, corn starch, clycerin, palm oil, xylitol, carrageenan, FD&C Yellow #6, FD&C Yellow #5, and natural and/or artificial flavors. An exemplary serving of this soft chew composition includes 250 mg quercetin, 250 mg vitamin C, 10 mg vitamin B3 (e.g., niacinamide), and 200 mcg folic acid. In another example, one serving of this soft chew composition contains 125 mg quercetin, 125 mg vitamin C, 5 mg vitamin B3, and 100 mcg folic acid. A subject can take one to eight servings (e.g., 4 servings) of this soft chew composition daily. The amounts taken can vary depending on, for example, the disorder or condition to be treated and the physical states of the subject.

The composition can include quercetin, vitamin C, vitamin B3, and folic acid as the only active ingredients. It also can further contain one or more other active ingredients, such as isoflavone (e.g., genistein or genistin), curcumin, resveratrol, isoquercetin, luteolin, epigallocatechin gallate (EGCG), CoQ10, eicosapentaenoic acid (EPA), and docosahexaenoic acid (DHA). These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, stevia and sucralose. The composition can also contain amino acids, fatty acids, proteins, fibers, minerals, a flavor enhancer, or a coloring agent. Exemplary amino acids include theanine (e.g., L-theanine) and alanine (e.g., L-alanine). Exemplary fatty acids include omega-3 fatty acids (e.g., linolenic acid), omega-6 fatty acids (e.g., linoleic acid), and omega-9 fatty acids (e.g., oleic acid). Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The composition used in the method of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

Alternatively, the composition can be a pharmaceutical composition containing a pharmaceutically acceptable carrier, i.e., a carrier that it is compatible with the active ingredient of the composition, and preferably, capable of stabilizing the active ingredient and not deleterious to the subject to be treated.

In the method of this invention, an effective amount of the composition is delivered to a subject via a conventional route of administration to improve his or her renal function. The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, intraperitoneal and intracranial injection, as well as various infusion techniques.

The compositions described above can be preliminarily screened for their efficacy in treating the above-described conditions by in vitro assays and then confirmed by animal experiments and clinic trials. Other suitable analytical and biological assays are apparent to those of ordinary skill in the art. For example, the bioavailability of quercetin can be measured by conducting pharmacokinetic studies and evaluated by the area under the curve in a plasma-drug concentration time curve.

Without further elaboration, it is believed that one skilled in the art can, based on the above description, utilize the present invention to its fullest extent. The following specific embodiment is, therefore, to be construed as merely illustrative, and not limitative of the remainder of the disclosure in any way whatsoever. All publications cited herein are incorporated by reference.

EXAMPLE

Increasing the Glomerular Filtration Rate with a Soft Chew Containing Quercetin, Vitamin C, Vitamin B3 and Folic Acid 501 subjects were randomly assigned to three groups, i.e., Group 1 (n=165), Group 2 (n=170), and Group 3 (n=166). Subjects in Group 1, Group 2, and Group 3 were administrated orally each day for 12 weeks with a placebo, soft chews (two chews each time, two times a day) providing 500 mg quercetin, 500 mg Vitamin C, 20 mg Vitamin B3, and 400 mcg folic acid, and soft chews providing 1000 mg quercetin, 1000 mg Vitamin C, 40 mg Vitamin B3, and 800 mcg folic acid. The kidney glomerular filtration rates (GFR) of these subjects were examined before and after treatment.

The GFRs of the subjects in Group 2 and Group 3 increase significantly relative to that of the subjects in Group 1, indicating that quercetin, vitamin C, vitamin B3. More specifically, while the GFR of Group 1 increased to a level of 2.61 ml/min after treatment was, the GFRs of Groups 2 and 3 increased to levels of 5.34 ml/min and 5.21 ml/min, respectively, after treatment (p=0.009). These results indicate that and quercetin, vitamin C, vitamin B3, and folic acid, in combination, improved renal function.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for increasing glomerular filtration rate, the method comprising identifying a subject in need of increased glomerular filtration rate and administering to the subject in need thereof an effective amount of a composition containing quercetin, vitamin C, vitamin B3, and folic acid.

2. The method of claim 1, wherein the composition has a weight ratio of 1:0.2-2.5:0.02-1:0.2-2 (mg/mg/mg/mcg) between quercetin, vitamin C, vitamin B3, and folic acid.

3. The method of claim 2, wherein the weight ratio is 1:0.5-1:0.02-0.2:0.5-1 (mg/mg/mg/mcg) between quercetin, vitamin C, vitamin B3, and folic acid.

4. The method of claim 3, wherein the weight ratio is 1:1:0.04:0.8 (mg/mg/mg/mcg).

5. The method of claim 1, wherein the effective amount of the composition is an amount that provides 500-2000 mg quercetin, 500-2000 mg vitamin C, 20-60 mg vitamin B3, and 400-800 mcg folic acid per day.

6. The method of claim 5, wherein the effective amount of the composition is an amount that provides 500 mg quercetin, 500 mg vitamin C, 20 mg vitamin B3, and 400 mcg folic acid per day.

7. The method of claim 5, wherein the effective amount of the composition is an amount that provides 1000 mg quercetin, 1000 mg vitamin C, 40 mg vitamin B3, and 800 mcg folic acid.

8. The method of claim 1, wherein the composition is in dry form.

9. The method of claim 1, wherein the composition is in liquid form.

10. The method of claim 1, wherein the composition is a food product.

11. The method of claim 10, wherein the food product is tea, juice, milk, coffee, a soft drink, jelly, ice cream, yogurt, cereal, chocolate, a cookie, or a snack bar.

12. The method of claim 1, wherein the composition is a dietary supplement or a pharmaceutical formulation.

13. The method of claim 12, wherein the composition is in the form of a tablet, a capsule, a soft chew, or a gel.

* * * * *